United States Patent
Kikuchi

(10) Patent No.: US 11,527,328 B2
(45) Date of Patent: Dec. 13, 2022

(54) INFORMATION PROCESSING APPARATUS, INFORMATION PROCESSING SYSTEM, INFORMATION PROCESSING METHOD, AND PROGRAM

(71) Applicant: CANON KABUSHIKI KAISHA, Tokyo (JP)

(72) Inventor: Toru Kikuchi, Ino (JP)

(73) Assignee: Canon Kabushiki Kaisha, Tokyo (JP)

( * ) Notice: Subject to any disclaimer, the term of this patent is extended or adjusted under 35 U.S.C. 154(b) by 280 days.

(21) Appl. No.: 16/767,093

(22) PCT Filed: Nov. 16, 2018

(86) PCT No.: PCT/JP2018/042398
§ 371 (c)(1),
(2) Date: May 26, 2020

(87) PCT Pub. No.: WO2019/107177
PCT Pub. Date: Jun. 6, 2019

(65) Prior Publication Data
US 2020/0381115 A1    Dec. 3, 2020

(30) Foreign Application Priority Data

Nov. 30, 2017    (JP) .............................. JP2017-230994

(51) Int. Cl.
*G06K 9/00*    (2022.01)
*G16H 50/20*    (2018.01)
(Continued)

(52) U.S. Cl.
CPC .......... *G16H 50/20* (2018.01); *G06T 7/0012* (2013.01); *G06T 7/62* (2017.01); *G16H 30/40* (2018.01);
(Continued)

(58) Field of Classification Search
CPC .......... G16H 50/20; G16H 30/40; G06T 7/62; G06T 7/0012; G06T 2207/20081; G06T 2207/30064; G06T 2207/30096
(Continued)

(56) References Cited

U.S. PATENT DOCUMENTS

| | | | |
|---|---|---|---|
| 2011/0213748 A1 | 9/2011 | Kawagishi et al. | |
| 2012/0008838 A1* | 1/2012 | Guyon | G16H 50/20 |
| | | | 382/128 |

(Continued)

FOREIGN PATENT DOCUMENTS

| | | |
|---|---|---|
| JP | 2012-94127 A | 5/2012 |
| JP | 2013-27635 A | 2/2013 |

(Continued)

OTHER PUBLICATIONS

Farhan, Saima, Muhammad Abuzar Fahiem, and Huma Tauseef. "An ensemble-of-classifiers based approach for early diagnosis of Alzheimer's disease: classification using structural features of brain images." Computational and mathematical methods in medicine 2014 (2014). (Year: 2014).*

(Continued)

*Primary Examiner* — Jonathan S Lee
(74) *Attorney, Agent, or Firm* — Canon U.S.A., Inc., IP Division

(57) ABSTRACT

An information processing method includes deducing a diagnosis name derived from a medical image on the basis of an image feature amount corresponding to a value indicating a feature of a medical image, deducing an image finding representing a feature of the medical image on the basis of the image feature amount, and presenting the image finding deduced in the deducing the image finding which is affected by an image feature amount common to the image feature amount that has affected the deduction of the diag- (Continued)

nosis name in the deducing the diagnosis name and the diagnosis name to a user.

17 Claims, 9 Drawing Sheets

(51) Int. Cl.
    *G06T 7/62*     (2017.01)
    *G16H 30/40*     (2018.01)
    *G06T 7/00*     (2017.01)

(52) U.S. Cl.
    CPC .............. *G06T 2207/20081* (2013.01); *G06T 2207/30064* (2013.01); *G06T 2207/30096* (2013.01)

(58) Field of Classification Search
    USPC ........................................................ 382/128
    See application file for complete search history.

(56) References Cited

U.S. PATENT DOCUMENTS

| | | |
|---|---|---|
| 2013/0051646 A1 | 9/2013 | Yokota |
| 2016/0022238 A1 | 1/2016 | Park et al. |
| 2016/0048737 A1 | 2/2016 | Kam et al. |
| 2016/0253466 A1 | 9/2016 | Agaian et al. |
| 2016/0335764 A1 | 11/2016 | Kawagishi et al. |
| 2020/0012904 A1* | 1/2020 | Zhao .................... G06V 20/20 |
| 2020/0242762 A1* | 7/2020 | Matsuki ............... G06K 9/6267 |

FOREIGN PATENT DOCUMENTS

| | | |
|---|---|---|
| JP | 2013-39230 A | 2/2013 |
| JP | 2018-166961 A | 11/2018 |
| WO | 2017/106645 A1 | 6/2017 |
| WO | 2017/179503 A1 | 10/2017 |

OTHER PUBLICATIONS

Choi, Jae Young, et al. "Classifier ensemble generation and selection with multiple feature representations for classification applications in computer-aided detection and diagnosis on mammography." Expert Systems with Applications 46 (2016): 106-121. (Year: 2016).*

Zhou Keyang et al., "Efficient Image Evidence Analysis of CNN Classification Results", [online], arXiv:1801.01693v1, Jan. 5, 2018.

Selvaraju R. Ramprasaath et al., "Grad-CAM:Visual Explanations from Deep Networks via Gradient-based Localization", [online], arXiv:1610.02391 v3, May 21, 2017.

Zeiler D. Matthew et al., "Visualizing and Understanding Convolutional Networks", [online], arXiv:1311.290lv3, Nov. 28, 2013.

Nappi J. Janne et al., "Deep transfer learning of virtual endoluminal views for the detection of polyps in CT colonography". Proc. of SPIE, Mar. 24, 2016, vol. 9785, 97852B.

Bar Yaniv et al., "Deep learning with non-medical training used for chest pathology identification", proc. of SPIE, vol. 9414, May 20, 2015,94140V.

* cited by examiner

FIG. 5

| IMAGE FINDING TYPE | IMAGE FINDING VALUE |
|---|---|
| SHAPE | GLOBULAR SHAPE |
| | NEARLY GLOBULAR SHAPE |
| | IRREGULAR SHAPE |
| | LOBULATED SHAPE |
| | ⋮ |
| SPICULA | PRESENT |
| | ABSENT |
| CAVITY | PRESENT |
| | ABSENT |
| ⋮ | ⋮ |

| DIAGNOSIS NAME |
|---|
| PRIMARY LUNG CANCER |
| METASTATIC LUNG CANCER |
| BENIGN NODE |

INFORMATION PROCESSING APPARATUS, INFORMATION PROCESSING SYSTEM, INFORMATION PROCESSING METHOD, AND PROGRAM

TECHNICAL FIELD

The disclosure of the present specification relates to an information processing apparatus, an information processing system, an information processing method, and a program.

BACKGROUND ART

A computer aided diagnosis (CAD) system has been proposed in which a medical image is analyzed by a calculator, and information is presented for assisting radiogram interpretation where a doctor observes the medical image and conducts a diagnosis. PTL 1 discloses a configuration in which information previously associated with a particular key word such as a diagnosis name is output to a report as reference information with respect to the diagnosis name.

According to the technology disclosed in PTL 1, there is a fear that, in the CAD system where the diagnosis name is deduced from the medical image, information that is not identified as the key word like information of an image finding related to the deduction is not to be presented as the reference information with respect to the diagnosis name in some cases.

CITATION LIST

Patent Literature

[PTL 1]
Japanese Patent Laid-Open No. 2012-94127

SUMMARY OF INVENTION

Solution to Problem

An information processing apparatus according to an aspect of the present invention includes a first deduction unit configured to deduce a diagnosis name derived from a medical image on a basis of an image feature amount corresponding to a value indicating a feature of the medical image, a second deduction unit configured to deduce an image finding representing the feature of the medical image on a basis of the image feature amount, and a presentation unit configured to present the image finding deduced by the second deduction unit affected by an image feature amount common to the image feature amount that has affected the deduction of the diagnosis name by the first deduction unit and the diagnosis name to a user.

Further features of the present invention will become apparent from the following description of exemplary embodiments with reference to the attached drawings.

BRIEF DESCRIPTION OF DRAWINGS

FIG. 5 illustrates examples of an image finding and a definition of data of a diagnosis name according to the first and second exemplary embodiments.

DESCRIPTION OF EMBODIMENTS

Figure 1:
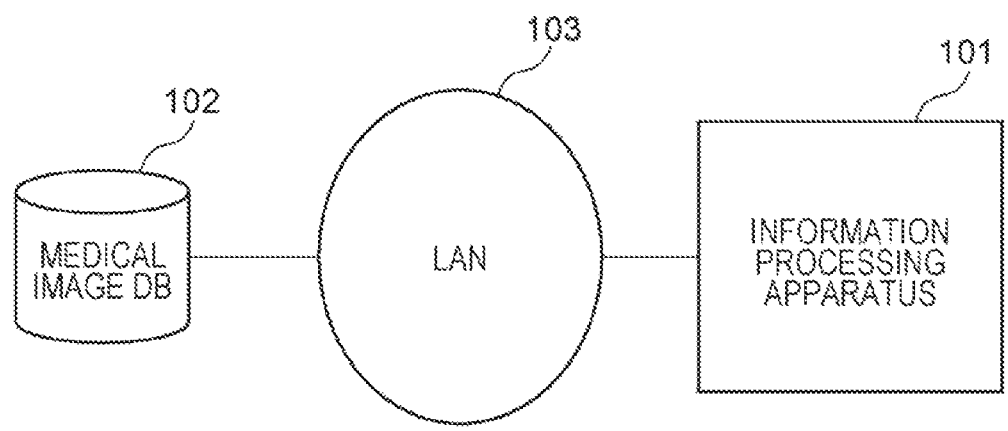
FIG. 1 illustrates an example of a system configuration of an information processing system including an information processing apparatus according to first and second exemplary embodiments.

Hereinafter, exemplary embodiments of the present invention will be described in detail with reference to the accompanying drawings. It should be noted that, unless particularly specified, items described according to another exemplary embodiment will be assigned with the same reference numerals, and descriptions thereof will be omitted. In addition, configurations illustrated in the following exemplary embodiments are merely examples, and the present invention is not to be limited to the illustrated configurations.

First Exemplary Embodiment

In a CAD system that deduces a diagnosis name from a medical image and presents the diagnosis name, a configuration is preferably adopted in which it is possible to grasp whether or not the diagnosis name presented as a deduction result is useful to a diagnosis by a doctor.

According to a first exemplary embodiment, descriptions will be provided of the information processing apparatus functioning as the CAD system that performs a deduction of a diagnosis name related to a lung node shadow on a chest X-ray computed tomography (CT) image. The information processing apparatus according to the present exemplary embodiment operates so as to display obtained medical image data, obtain a lesion position on the basis of an input by a user, perform the deduction of the diagnosis name from the image with respect to the obtained lesion position, and present the diagnosis name and an image finding serving as reference information.

System Configuration

FIG. 1 is a system configuration diagram of an information processing system including an information processing apparatus 101 according to the present exemplary embodiment.

In FIG. 1, the information processing system is constituted by a medical image database (hereinafter, which will be referred to as a medical image DB) 102, the information processing apparatus 101, and a local area network (LAN) 103.

The medical image DB 102 stores medical image data obtained by an imaging device such as a computed tomography (CT) device. The medical image DB 102 also provides a related-art database function for searching for and obtaining the medical image data via the LAN 103.

Hardware Configuration

Figure 2:
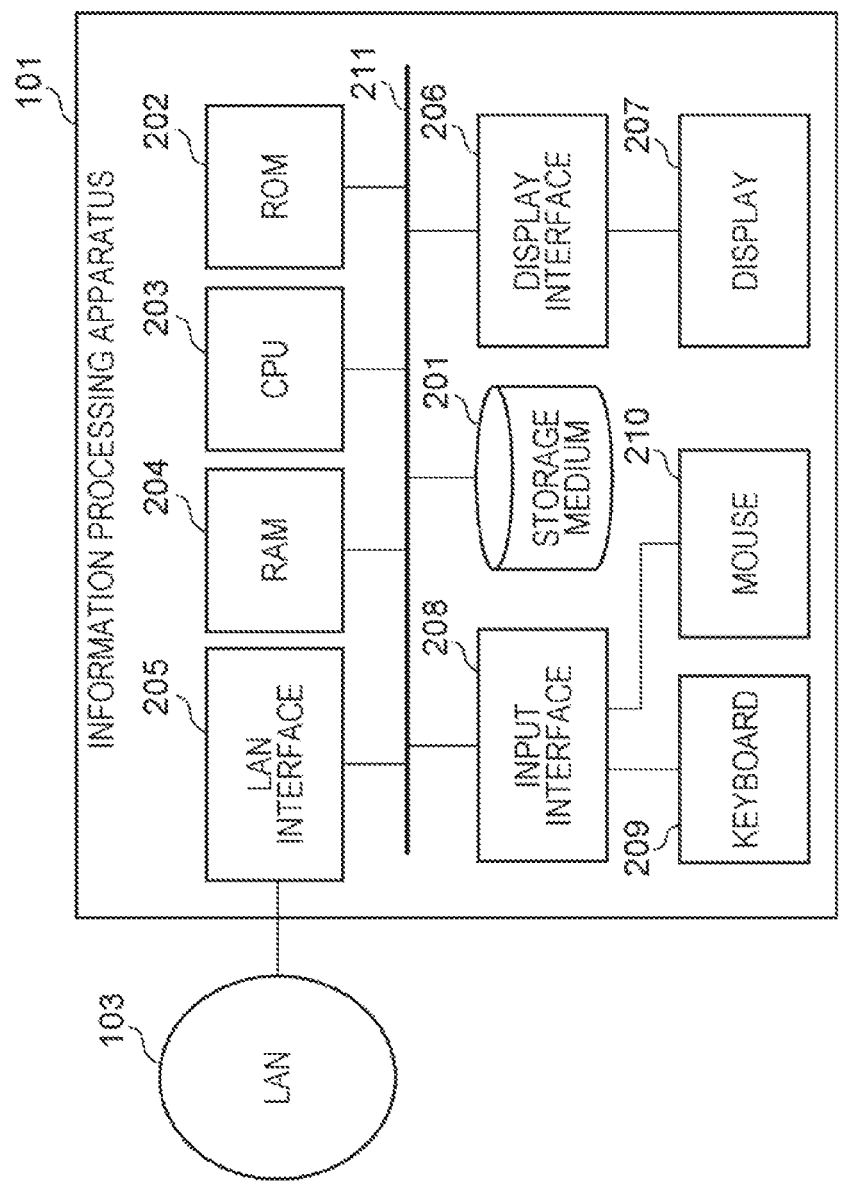
FIG. 2 illustrates an example of a hardware configuration of the information processing apparatus according to the first and second exemplary embodiments.

FIG. 2 is a hardware configuration diagram of the information processing apparatus 101 according to the present exemplary embodiment.

In FIG. 2, a storage medium 201 is a storage medium such as a hard disk drive (HDD) that stores an operating system (OS), processing programs for performing various processes according to the present exemplary embodiment, and various pieces of information. A read only memory (ROM) 202 stores a program such as a basic input output system (BIOS) for initializing hardware and activating the OS. A central processing unit (CPU) 203 performs calculation processing when the BIOS, the OS, or the processing program is executed. A random access memory (RAM) 204 temporarily stores information to be used when the CPU 203 executes the program. A LAN interface 205 is an interface that is compatible with a standard such as Institute of Electrical and Electronics Engineers (IEEE) 802.3ab and performs a communication via the LAN 103. A display 207 displays a display screen, and a display interface 206 is a display interface that converts screen information to be displayed on the display 207 into a signal and outputs the signal. A keyboard 209 is used to perform a key input. A mouse 210 is used to specify a coordinate position on the screen and perform an input of a button operation associated with an image position. An input interface 208 is configured to receive signals from the keyboard 209 and the mouse 210. Respective blocks perform communications via an internal bus 211. The CPU 203 is an example of a processor. The information processing apparatus 101 may also include at least one of a GPU or a field-programmable gate array (FPGA) in addition to the CPU 203. The information processing apparatus 101 may also include a GPU or an FPGA that dedicatedly performs the processing related to the deduction. The ROM 202 and the RAM 204 are examples of a memory.

Configuration of Medical Image Data

Figure 4:
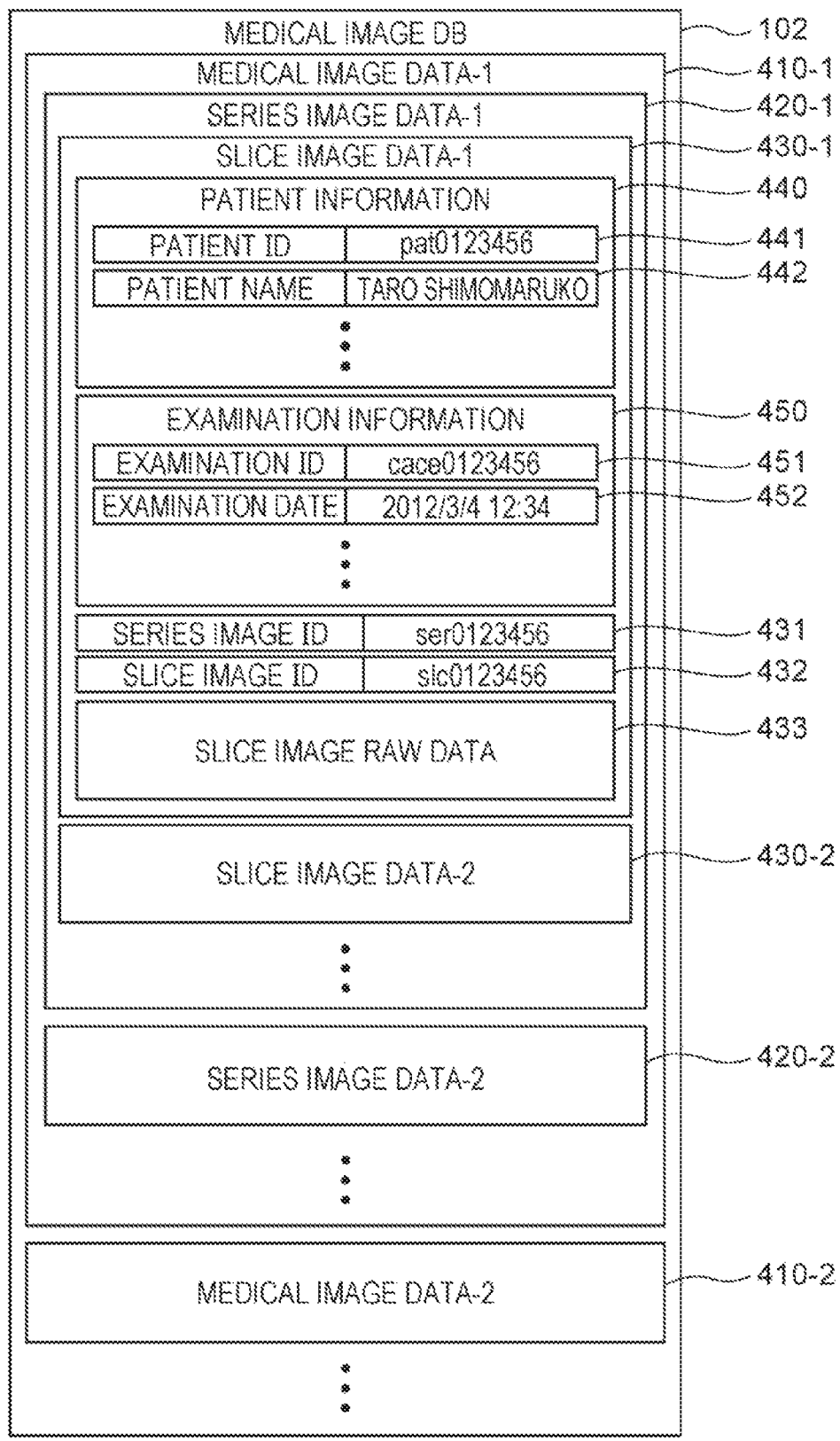
FIG. 4 illustrates an example of a configuration of medical image data according to the first and second exemplary embodiments.

FIG. 4 illustrates an example of a configuration of the medical image data stored in the medical image DB 102.

In FIG. 4, plural pieces of medical image data 410-$i$ (i=1, . . . , Ni) are stored in the medical image DB 102 and constituted by plural pieces of series image data 420-$i$ (i=1, . . . , Nsr). Furthermore, the series image data 420-$i$ (i=1, . . . , Nsr) is constituted by plural pieces of slice image data 430-$i$ (i=1, . . . , Nsl). Furthermore, the slice image data 430-$i$ (i=1, . . . , Nsl) is constituted by patient information 440, examination information 450, a series image identifier (which will be hereinafter referred to as an ID) 431, a slice image ID 432, and slice image RAW data 433. Herein, the slice image ID 432 is an identifier for uniquely identifying a single tomographic image, and the series image ID 431 is an identifier for uniquely identifying a plurality of slice images obtained by single imaging. In the example of FIG. 4, a value of the series image ID 431 is set as "ser0123456", and a value of the slice image ID 432 is set as "slc0123456". The slice image RAW data 433 is data in which pixel values of the slice images are arranged in a predetermined order. The patient information 440 is constituted by a patient ID 441, a patient name 442, and other information related to the patient of this case which is not illustrated in the drawing. In the example of FIG. 4, a value of the patient ID 441 is set as "pat0123456", and a value of the patient name 442 is set as "Taro Shimomaruko". The examination information 450 is constituted by an examination ID 451, an examination date 452, and other information related to the examination of this case which is not illustrated in the drawing. In the example of FIG. 4, a value of the examination ID 451 is set as "case0123456", and a value of the examination date 452 is set as "2012 Mar. 4 12:34".

Examples of Image Finding and Definition of Data of Diagnosis Name

FIG. 5 illustrates examples of an image finding and a definition of the diagnosis name according to the present exemplary embodiment.

In FIG. 5, information 501 defines a type and a value of an image finding which will be referred to as an image finding 501, and information 502 defines a value of a diagnosis name which will be referred to as a diagnosis name 502. The image finding 501 is constituted by an image finding type and an image finding value. The image finding value is a phrase representing a feature related to the image finding type depicted in a certain medical image. The example of FIG. 5 indicates that the image finding value is set as one of "globular shape", "nearly globular shape", "irregular shape", "lobulated shape", and the like in a case where the image finding type is "shape", and the image finding value indicates one of "present" and "absent" in a case where the image finding type is "spicula" or "cavity". With regard to the diagnosis name 502, the example of FIG. 5 also indicates that the value of the diagnosis name is set as one of "primary lung cancer", "metastatic lung cancer", and "benign node".

Display Screen

Figure 6:
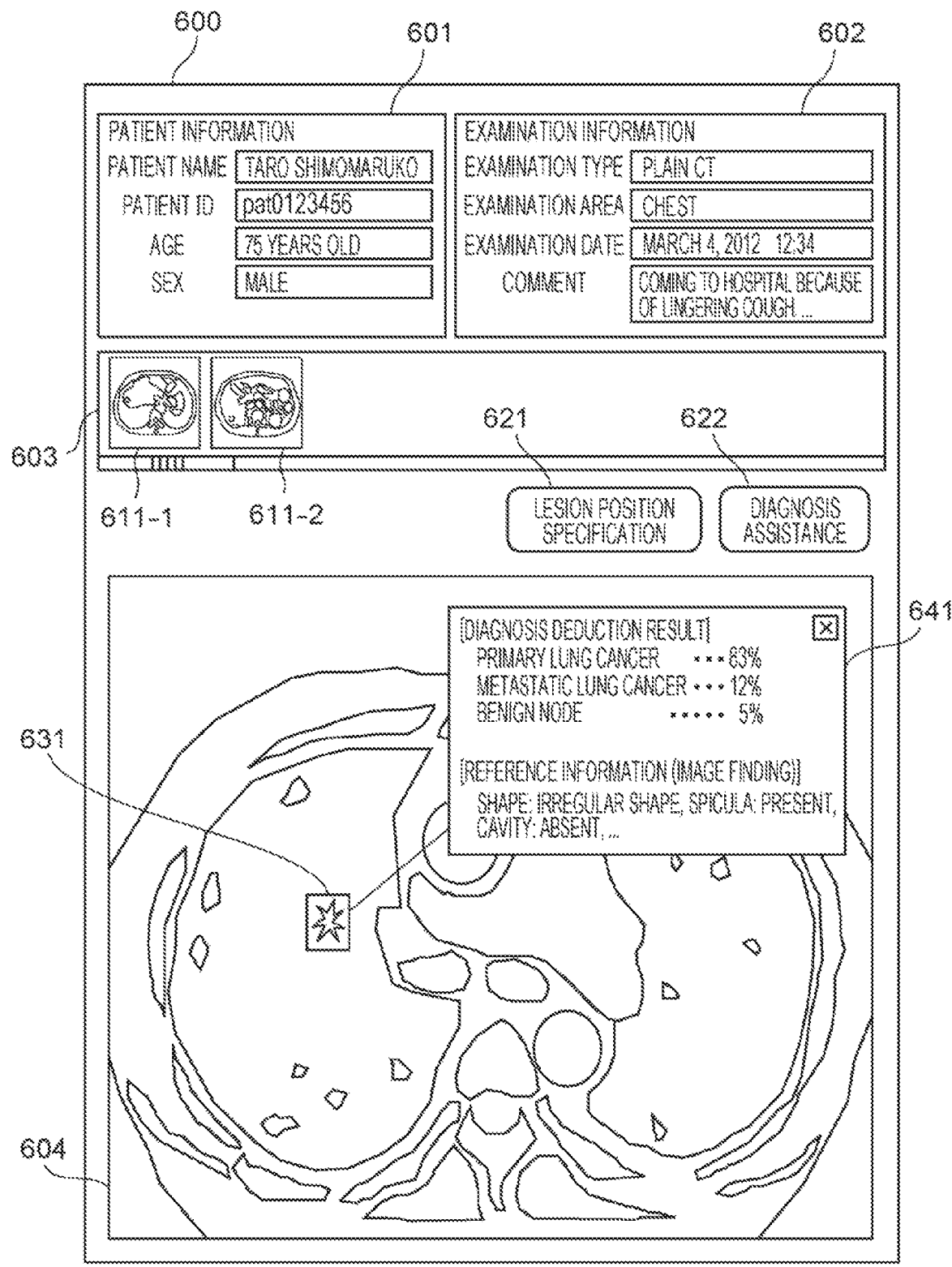
FIG. 6 illustrates an example of a screen displayed by the information processing apparatus according to the first and second exemplary embodiments.

FIG. 6 illustrates an example of a display screen of the information processing apparatus 101 according to the present exemplary embodiment.

In FIG. 6, a display screen 600 is a user interface screen displayed on the display 207. The display screen 600 is constituted by a patient information display area 601, an examination information display area 602, a series image display area 603, an image display area 604, a lesion position specification button 621, and a diagnosis assistance button 622.

Information related to the patient information 440 of the medical image data 410-$i$ (i=1, . . . , Ni) is displayed in the patient information display area 601. In the example of FIG. 6, a patient name is set as "Taro Shimomaruko", a patient ID is set as "pat0123456", the age is set as "75 years old", and the sex is set as "male".

Information related to the examination information 450 of the medical image data 410-$i$ (i=1, . . . , Ni) is displayed in the examination information display area 602. In the example of FIG. 6, the examination type is set as "plain CT", the examination area is set as "chest", the examination date is set as "Mar. 4, 2012 12:34", and the comment is set as "coming to hospital because of lingering cough . . . .".

A reduced image 611-$i$ (i=1, . . . , Nsr) of the initial slice image RAW data 433 for each of the series image data 420-$i$ (i=1, . . . , Nsr) of the medical image data 410-$i$ (i=1, . . . , Ni) is displayed in the series image display area 603.

The slice image RAW data 433 of the series image data 420-$i$ (i=1, ..., Nsr) corresponding to the reduced image 611-$i$ (i=1, ..., Nsr) selected in the series image display area 603 is displayed in the image display area 604. In addition, scrolling of the displayed slice image and changing of the display such as a change in a grayscale display condition called window level (WL)/window width (WW) and the like can be performed.

The lesion position specification button 621 is a button for specifying a lesion position in the image display area 604. The lesion position specification button 621 is clicked by the mouse, and a lesion position 631 can be specified by performing mouse dragging on the image display area 604.

The diagnosis assistance button 622 is a button for performing the deduction of the diagnosis name from an image of the lesion position 631. When the diagnosis assistance button 622 is clicked by using the mouse, the deduction of the diagnosis name is performed from the image of the lesion position 631, and a diagnosis assistance result 641 is displayed together with the image finding serving as the reference information. In the example of FIG. 6, it is displayed in the diagnosis assistance result 641 that a probability of the primary lung cancer is "83%", a probability of the metastatic lung cancer is "12%", and a probability of the benign node is "5%" as the diagnosis deduction result, and "shape: irregular shape", "spicula: present", and "cavity: absent" are displayed in the image finding serving as the reference information with respect to this deduction result.

Function Block 1

Figure 3:
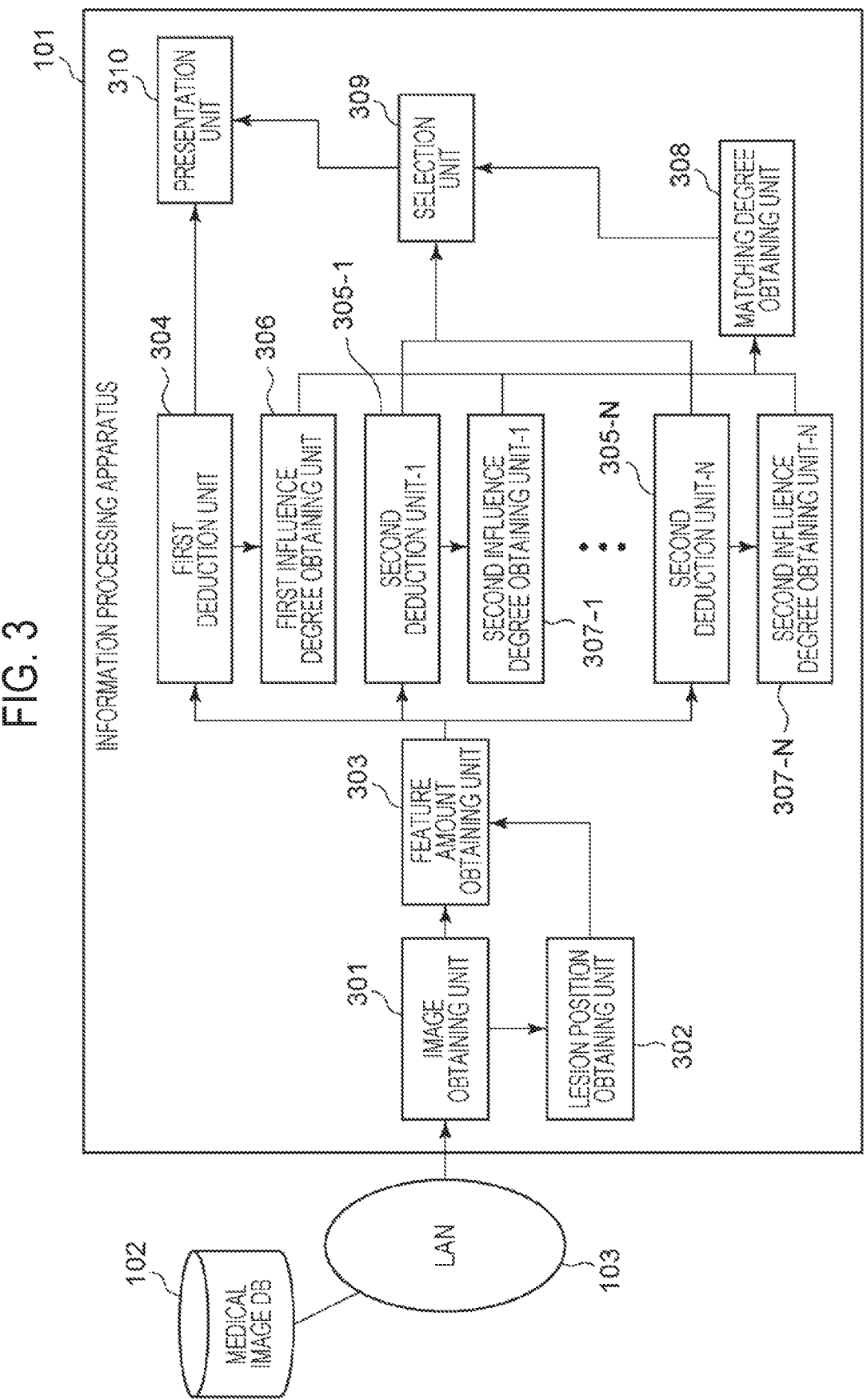
FIG. 3 illustrates an example of a functional block of the information processing apparatus according to the first and second exemplary embodiments.

FIG. 3 is a functional block diagram of the information processing apparatus 101 according to the present exemplary embodiment.

In FIG. 3, the information processing apparatus 101 includes an image obtaining unit 301, a lesion position obtaining unit 302, a feature amount obtaining unit 303, a first deduction unit 304, and second deduction units 305-$i$ (i=1, ..., Nf). The information processing apparatus 101 further includes a first influence degree obtaining unit 306, second influence degree obtaining units 307-$i$ (i=1, ..., Nf), a matching degree obtaining unit 308, a selection unit 309, and a presentation unit 310.

The image obtaining unit 301 obtains the medical image data 410-$i$ (i=1, ..., Ni) from the medical image DB 102 via the LAN 103.

The lesion position obtaining unit 302 displays the medical image data 410-$i$ (i=1, ..., Ni) obtained by the image obtaining unit 301 on the display screen 600 and accepts the specification of the lesion position 631 by the user. According to another exemplary embodiment, the lesion position obtaining unit 302 performs image processing with respect to the medical image data 410-$i$ and extracts the lesion position 631. The feature amount obtaining unit 303 obtains an image feature amount of the medical image data 410-$i$ (i=1, ..., Ni) of the lesion position 631.

The first deduction unit 304 deduces the diagnosis name on the basis of the image feature amount obtained by the feature amount obtaining unit 303, and the second deduction units 305-$i$ (i=1, ..., Nf) respectively deduce the image finding values on the basis of the obtained image feature amount. The first deduction unit 304 is an example of a first deduction unit that deduces the diagnosis name derived from the medical image on the basis of the image feature amount corresponding to a value indicating a feature of the medical image. The second deduction unit 305-$i$ (i=1, ..., Nf) perform the deduction of the image finding value for each of the image finding types. The second deduction units 305-$i$ are deduction units that provide a classification of the image finding value related to one of mutually different image finding types. Nf denotes the number of the image finding types for which the deduction is performed. When the deduction unit that performs the deduction of the image finding value for each of the image finding types is provided, as compared with a case where the single deduction unit performs the deduction by combining the image finding values of the plurality of image finding types, the second deduction units 305-$i$ can respectively decrease the number of output nodes. The second deduction units 305-$i$ are an example of a second deduction unit that deduces the image finding corresponding to a phrase representing a feature of the medical image on the basis of the image feature amount corresponding to a value indicating a feature of the medical image. Details of the feature amount obtaining unit 303, the first deduction unit 304, and the second deduction units 305-$i$ (i=1, ..., Nf) will be described below with reference to FIG. 9.

According to another exemplary embodiment, part of the processing in the second deduction units 305-$i$ may be the same in the respective deductions related to the image finding types. According to another one of the exemplary embodiments, the second deduction units 305 may be constituted by including a deduction device or reasoner that provides classifications of the image finding values related to the plurality of image finding types.

Feature Amount Obtaining Unit, Deduction Unit

Figure 9:
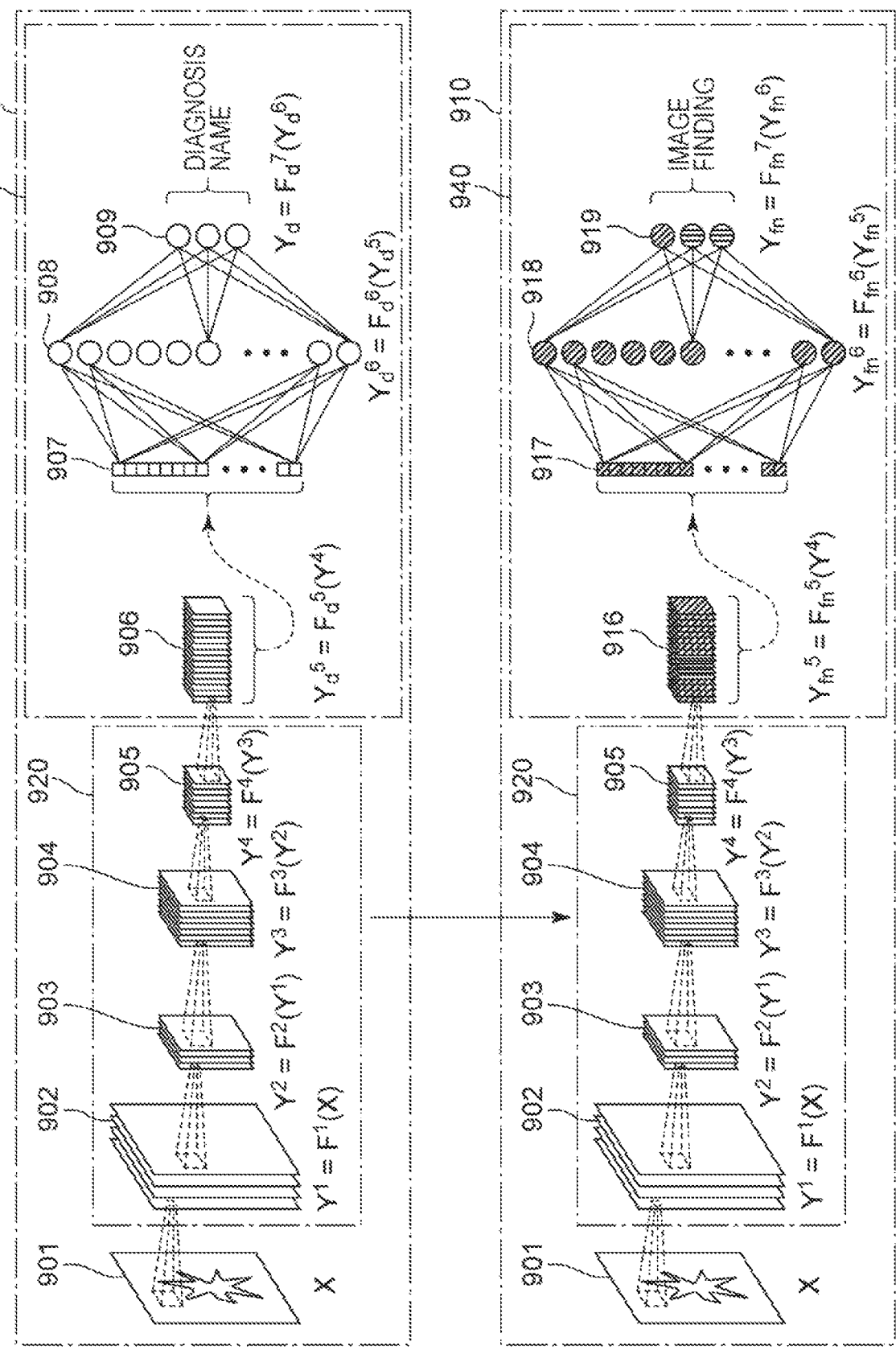
FIG. 9 is an explanatory diagram for describing an example of a feature amount obtaining unit and a deduction unit of the information processing apparatus according to the first and second exemplary embodiments.

FIG. 9 illustrates a concept of the feature amount obtaining unit 303, the first deduction unit 304, and the second deduction units 305-$i$ (i=1, ..., Nf) according to the present exemplary embodiment. The feature amount obtaining unit 303, the first deduction unit 304, and the second deduction units 305-$i$ (i=1, ..., Nf) are constituted by using a related-art multi-layer convolutional neural networks (CNN).

FIG. 9 illustrates a concept of the CNN 900 obtained by machine learning so as to deduce the diagnosis name from the image and a concept of the CNN 910 obtained by machine learning so as to deduce the image finding (image finding value) from the image. FIG. 9 also illustrates an image 901 input to the CNN, outputs 902, 904, 906, and 916 of a convolutional layer, and outputs 903 and 905 of a pooling layer. FIG. 9 also illustrates states 907 and 917 in which the outputs 906 and 916 are respectively arranged in a one-dimensional manner, a fully connected layer 908, and output layers 909 and 919 corresponding to the deduction result of the class classification.

Herein, according to the present exemplary embodiment, the CNN 910 that deduces the image finding from the image is constituted by performing transfer learning of the CNN 900 that deduces the diagnosis name from the image. The transfer learning refers to a configuration in which a parameter of a layer in an upstream stage of the CNN is fixed, and only a layer in a downstream stage is caused to perform learning with respect to another problem. FIG. 9 illustrates that a range 920 from the output 902 to the output 905 corresponding to the layers in the upstream stage of the network where the learning is performed so as to deduce the diagnosis name is fixed, and a range 940 from the output 916 to the output layer 919 in and after the stage of the output 905 where the learning is performed so as to deduce the image finding.

In the CNN having the above-described configuration, the feature amount obtaining unit 303 corresponds to processing in the range 920, the first deduction unit 304 corresponds to processing in a range 930, and the second deduction units 305-$i$ ($i$=1, . . . , Nf) corresponds to processing in the range 940.

That is, the CNN 900 is configured by including the range 920 and the range 930. The range 920 corresponds to the feature amount obtaining unit 303, and the range 930 corresponds to the first deduction unit 304. The CNN 900 is an example of a third deduction unit that deduces the diagnosis name 909 from the medical image 901, and the third deduction unit is configured by including the first deduction unit. In more detail, the image feature amount input to the first deduction unit 304 is a value obtained in a predetermined stage included in the deduction process in the CNN 900 (the third deduction unit), and the first deduction unit performs the deduction in the deduction process in and after the predetermined stage in the third deduction unit.

The CNN 910 is configured by including the range 920 and the range 940. The range 920 corresponds to the feature amount obtaining unit 303, and the range 940 corresponds to one of the second deduction units 305-$i$. The CNN 910 is an example of a fourth deduction unit that deduces the image finding 919 from the medical image 901, and the fourth deduction unit is configured by including the second deduction unit. As described above, the CNN 910 is obtained by performing the transfer learning of the CNN 900. In more detail, the CNN 910 (fourth deduction unit) has the common deduction process up to the predetermined stage (the range 920) in the CNN 900 (third deduction unit). Then, the second deduction unit performs the deduction in the deduction process in and after the predetermined stage in the CNN 910 (fourth deduction unit).

It should be noted that the stage in the deduction process (order of the processes in the respective layers) is represented as l, an output value in the l-th layer is represented as $Y^l$, and processing in the l-th layer is represented as $Y^l = F^l(Y^{l-1})$. The 1st layer is represented as $Y^1 = F^1(X)$, and the final stage is represented as $Y = F^7(Y^6)$. The processing in the range 930 is assigned with a subscript "d", and the processing in the range 940 is assigned with a subscript "fn" ($n$=1, . . . , Nf) for each image finding.

Function Block 2

With reference to FIG. 3 again, the first influence degree obtaining unit 306, the second influence degree obtaining units 307-$i$ ($i$=1, . . . , Nf), the matching degree obtaining unit 308, the selection unit 309, and the presentation unit 310 will be described.

The first influence degree obtaining unit 306 obtains an influence degree (first influence degree) corresponding to a degree of the influence of the image feature amount with respect to the deduction result of the first deduction unit 304. A classification result is set as Cd, a layer where the image feature amount is obtained is set as the l-th layer, a channel number of the output of the layer is set as k, an output value of elements (i, j) of the channel k of the layer in the l-th stage is set as $Y_{ij}^{l,k}$, and an output value of the final layer corresponding to the classification result Cd is set as $y_d^{Cd}$. (i, j) denote coordinates of the image output by the layer in the l-th stage, and its maximum values ($i_{max}$, $j_{max}$) correspond to an image size. In FIG. 9, $y_d^{Cd}$ denotes an output value of one of nodes (one of circles 909) of the output layer 909 corresponding to the classification result Cd. $Y_{ij}^{l,k}$ denotes an output value of the k-th (k-th among a plurality of squares 903 or 905) coordinates (i, j) of the output of the pooling layer (903 in the case of l=1 or 905 in the case of l=3). The first influence degree $\alpha_d^k$ of the channel k is obtained by Expression 1.

[Math. 1]

$$\alpha_d^k = \frac{1}{Z} \Sigma_i \Sigma_j \frac{\partial y_d^{Cd}}{\partial Y_{ij}^{l,k}} \quad (1)$$

It should be noted that Z denotes a product of $i_{max}$ and $j_{max}$, Cd=0 represents the primary lung cancer, 1 represents the metastatic lung cancer, and 2 represents the benign node. The output value $Y_{ij}^{l,k}$ of the channel k of the layer in the l-th stage is set as the image feature amount. Expression 1 calculates a degree of change in the deduction result in a case where the output value of the channel k changes. In more detail, Expression 1 indicates an average of the entire filter of the change amount of the deduction result when the respective element values of the output of the channel k change. The first influence degree obtaining unit 306 is an example of a first obtaining unit that obtains a degree of the influence at which the image feature amount affects the deduction result by the first deduction unit 304 (first deduction unit).

Similarly, the second influence degree obtaining units 307-$i$ ($i$=1, . . . , Nf) obtains an influence degree (second influence degree) of the image feature amount with respect to the deduction result of the second deduction units 305-$i$ ($i$=1, . . . , Nf). When an output value of the final layer corresponding to the classification result Cfn is set as $y_{fn}^{Cfn}$, the second influence degree $\alpha_{fn}^k$ of the channel k is obtained by Expression 2.

[Math. 2]

$$\alpha_{fn}^k = \frac{1}{Z} \Sigma_i \Sigma_j \frac{\partial y_{fn}^{cfn}}{\partial Y_{ij}^{l,k}} \quad (2)$$

It should be noted that, with regard to Cfn, for example, in a case where the image finding type is the shape, 0 denotes globular shape, 1 denotes nearly globular shape, 2 denotes irregular shape, and 3 denotes lobulated shape, . . . . The second influence degree obtaining units 307-$i$ is an example of a second obtaining unit that obtains a second influence degree corresponding to a degree of the influence at which the image feature amount affects the deduction result by the second deduction units 305-$i$ (second deduction unit). In FIG. 9, $y_{fn}^{Cfn}$ denotes an output value of one of the nodes (one of circles 919) of the output layer 919 corresponding to the classification result Cfn.

The matching degree obtaining unit 308 obtains a matching degree $P_{sn}$ between the second influence degree $\alpha_{fn}^k$ and the first influence degree $\alpha_d^k$ with regard to each of the image finding types ($n$=1, . . . , Nf) from Expression 3.

[Math. 3]

$$P_{sn} = \frac{N_{sn}}{N_f} \quad (3)$$

Where $N_{sn}$ denotes the number of the channels k in which both the first influence degree $\alpha_d^k$ and the second influence degree $\alpha_{fn}^k$ exceed the predetermined constant $a_1$ and is obtained by Expression 4.

[Math. 4]

$$N_{sn} = \text{count}(k|\alpha_d^k > a_1 \text{ and } \alpha_{fn}^k > a_1) \qquad (4)$$

Where count (A|B) represents the number of A satisfying a condition B. The matching degree obtaining unit 308 is an example of a third obtaining unit that obtains a matching degree corresponding to a degree of matching between the image feature amount affecting the deduction result by the first deduction unit 304 (first deduction unit) and the image feature amount affecting the deduction result by the second deduction units 305-i (the second deduction unit) on the basis of the first influence degree and the second influence degree.

The selection unit 309 selects a predetermined number of the image finding types having high matching degrees $P_{sn}$ (higher than others). When the image finding type is selected, the image finding values deduced by the second deduction units 305-i corresponding to the image finding types are selected. The predetermined number can be specified by a setting by the user which is not illustrated in the drawing. The matching degree is determined on the basis of the first influence degree and the second influence degree. The selection unit 309 is an example of a selection unit that selects the image finding on the basis of the matching degree that is obtained on the basis of the first influence degree and the second influence degree.

The presentation unit 310 creates the diagnosis assistance result 641 from the diagnosis name that is the deduction result of the first deduction unit 304 and the image finding that is the deduction result of the second deduction units 305-i (i=1, . . . , Nf) corresponding to the image finding type selected by the selection unit 309. In the diagnosis assistance result 641, the selected image finding is arranged as the reference information (associated information) with respect to the diagnosis name of the deduction result. The presentation unit 310 also arranges the diagnosis assistance result 641 on the display screen 600 to be displayed on the display 207. According to one of the exemplary embodiments, the presentation unit 310 individually presents the reference information with respect to each of a plurality of diagnosis names. According to another one of the exemplary embodiments, the presentation unit 310 presents reference information with respect to a particular diagnosis name such as, for example, a diagnosis name having a high degree of urgency. With this configuration, the image finding deduced by being affected by the image feature amount common to the image feature amount affecting the deduction of the diagnosis name is presented. The presentation unit 310 is an example of a presentation unit that presents the image finding and the diagnosis name to the user.

Main Processing

Figure 7:
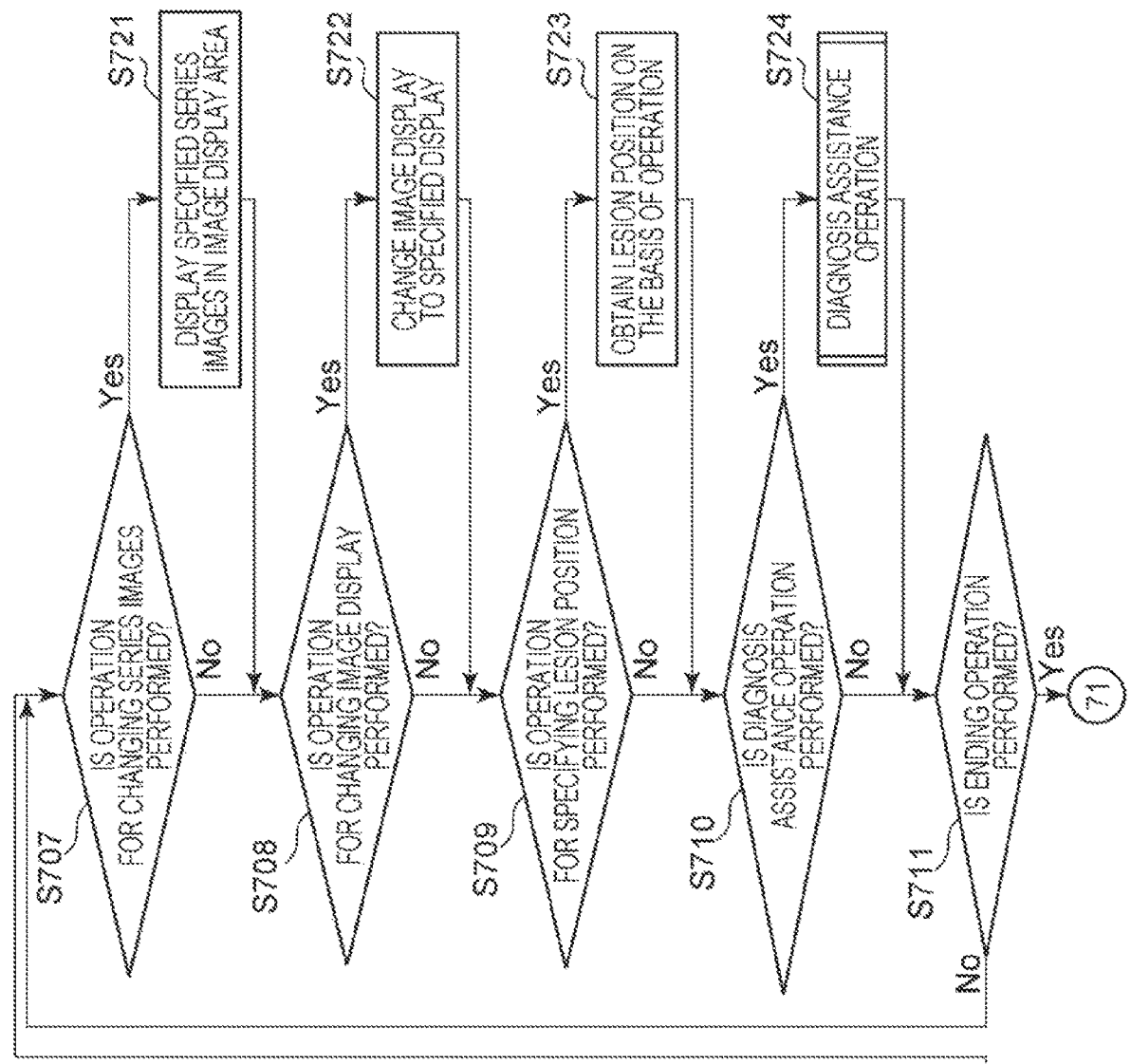
FIG. 7 is a flow chart illustrating an example of processing performed by the information processing apparatus according to the first and second exemplary embodiments.

FIG. 7 is a flow chart illustrating an example of processing performed by the information processing apparatus 101 according to the present exemplary embodiment. The main processing performed by the information processing apparatus 101 is started at the beginning after the activation of the information processing apparatus 101. When the processing is started, in step S701, the image obtaining unit 301 receives a specification of an examination ID by a user interface that is not illustrated in the drawing by the user.

Next, in step S702, the image obtaining unit 301 obtains the medical image data 410-i (i=1, . . . , Ni) from the medical image DB 102 on the basis of the examination ID.

In step S703, the lesion position obtaining unit 302 displays the patient information 440 of the obtained medical image data 410-i (i=1, . . . , Ni) on the patient information display area 601. In step S704, the lesion position obtaining unit 302 displays the examination information 450 on the examination information display area 602. In step S705, the lesion position obtaining unit 302 displays initial images of the respective series image data 420-i (i=1, . . . , Nsr) of the medical image data 410-i (i=1, . . . , Ni) in the series image display area 603 as representative images of the respective series image data. In step S706, the lesion position obtaining unit 302 displays one initial piece of the series image data 420-i (i=1, . . . , Nsr) such as, for example, the series image data 420-1 in the image display area 604.

In step S707, the lesion position obtaining unit 302 determines whether or not the user performs an operation for changing the series image. In step S707, in a case where the change operation of the series image is detected (S707: Yes), the lesion position obtaining unit 302 displays the series image data 420-i (i=1, . . . , Nsr) specified by the change operation in the image display area 604 in step S721. Herein, the change operation of the series image refers to a double click operation of a left button of the mouse on the reduce image 611-i (i=1, . . . , Nsr) of the series image. In step S707, in a case where the change operation of the series image is not detected (S707: No) or the processing is ended in step S721, the flow proceeds to step S708.

In step S708, the lesion position obtaining unit 302 determines whether or not the user performs an operation for changing the image display. In step S708, in a case where the change operation of the image display is detected (S708: Yes), the lesion position obtaining unit 302 changes the image display displayed in the image display area 604 into the specified display in step S722. Herein, the display operation refers to a change operation in which a scroll operation of the images is based on rotation of a mouse wheel (for changing a slice position of the image to be displayed), press of up and down arrow keys corresponds to WL, and press of left and right arrow keys corresponds to WW. In step S708, in a case where the change operation of the image display is not detected (S708: No) or the processing in step S722 is ended, the flow proceeds to step S709.

In step S709, the lesion position obtaining unit 302 determines whether or not the user performs an operation for specifying the lesion position. In step S709, in a case where the specification operation of the lesion position is detected (S709: Yes), the lesion position obtaining unit 302 obtains the lesion position 631 on the basis of the operation by the user in step S723. Herein, the specification operation of the lesion position is a drag operation of the left button of the mouse in the image display area 604 after the click operation of the left button of the mouse on the lesion position specification button 621. In step S709, in a case where the specification operation of the lesion position is not detected (S709: No) or the processing in step S723 is ended, the flow proceeds to step S710.

In step S710, the lesion position obtaining unit 302 determines whether or not the user performs an operation for specifying diagnosis assistance. In step S710, in a case where the diagnosis assistance operation is detected (S710: Yes), the flow proceeds to step S724. A detail of the diagnosis assistance processing in step S724 will be described with reference to FIG. 8. Herein, the diagnosis assistance operation refers to a click operation of the left button of the mouse of the diagnosis assistance button 622. In step S710, in a case where the diagnosis assistance operation is not detected (S710: No) or the processing in step S724 is ended, the flow proceeds to step S711.

In step S711, the lesion position obtaining unit 302 determines whether or not the user performs an operation for ending the process. In step S711, in a case where the ending operation is detected (S711: Yes), the flow returns to step S701, and the information processing apparatus 101 accepts the specification of the examination ID. In a case where the ending operation is not detected (S711: No), the flow returns to step S707, and the information processing apparatus 101 repeatedly performs the detection of the operation by the user. Herein, the ending operation refers to an operation for closing a window provided by the general OS.

It should be noted that the case has been described where the lesion position obtaining unit 302 performs the processes in steps S703 to S711, S721, S722, and S723 as an example, but the present exemplary embodiment is not limited to this configuration. For example, a display control unit (not illustrated) may perform at least part of the processes for causing the display 207 to display the medical image or the like in steps S703 to S706, S721, and S722 instead of the lesion position obtaining unit 302. In addition, a determination unit (not illustrated) may perform at least part of the processes for determining the presence or absence of the particular operation input by the user in steps S707 to S711 instead of the lesion position obtaining unit 302.

Diagnosis Assistance Processing

Figure 8:
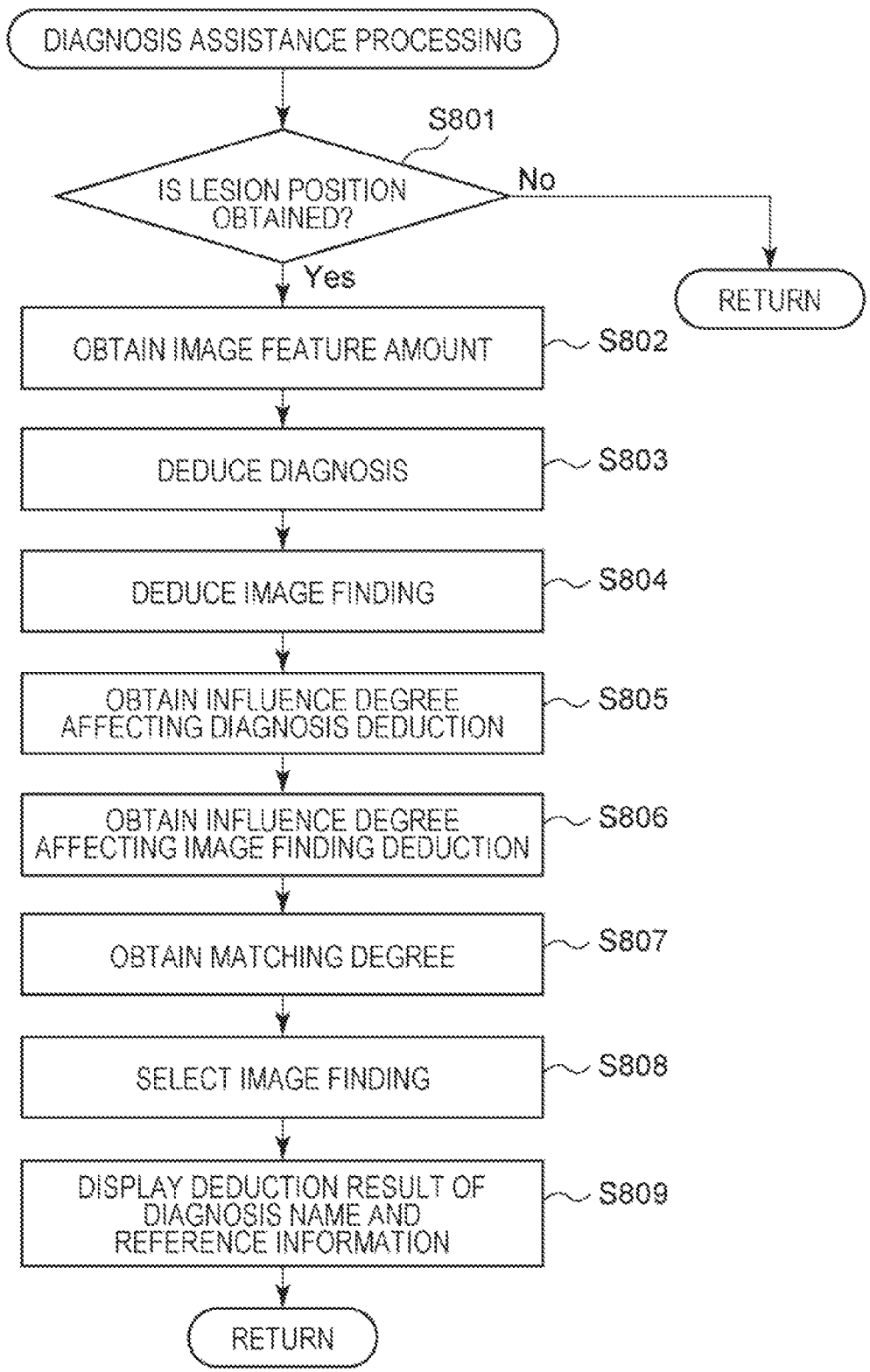
FIG. 8 is a flow chart illustrating an example of processing performed by the information processing apparatus according to the first and second exemplary embodiments.

FIG. 8 is a flow chart illustrating an example of processing performed by the information processing apparatus 101 according to the present exemplary embodiment. An example of the diagnosis assistance processing performed in step S724 of the main processing will be described with reference to FIG. 8. In step S801, in a case where the obtainment of the lesion position 631 is confirmed (S801: Yes), the feature amount obtaining unit 303 obtains the image feature amount from the image of the obtained lesion position in step S802. Next, in step S803, the first deduction unit 304 performs the deduction of the diagnosis name on the basis of the obtained image feature amount. Next, in step S804, each of the second deduction units 305-$i$ ($i=1, \ldots, Nf$) deduces the image finding on the basis of the obtained image feature amount.

In step S805, the first influence degree obtaining unit 306 obtains the first influence degree $\alpha_d^k$ by the above-described Expression 1. Next, in step S806, the second influence degree obtaining unit 307-$i$ ($i=1, \ldots, Nf$) obtains the second influence degree $\alpha_{fn}^k$ by the above-described Expression 2.

In step S807, the matching degree obtaining unit 308 obtains the matching degree $P_{sn}$ by the above-described Expression 3. Next, in step S808, the selection unit 309 selects the image finding type on the basis of the matching degree $P_{sn}$.

In step S809, the presentation unit 310 creates the diagnosis assistance result 641 from the deduced diagnosis name and the image finding selected by the selection unit 309 to be displayed on the display screen 600. Then, the flow returns to the main processing of FIG. 7. On the other hand, in step S801, in a case where the obtainment of the lesion position 631 is not confirmed (S801: No), the flow returns to the main processing without performing the processing.

As described above, according to the present exemplary embodiment, even in a case where the diagnosis name is deduced from the medical image, since the image finding highly affecting the deduction result of the diagnosis name can be presented as the reference information, the doctor can determine whether or not the deduction result is useful to the diagnosis.

Modified Example of First Exemplary Embodiment

The feature amount obtaining unit 303 according to the first exemplary embodiment may obtain a general image feature amount such as SIFT, SURF, or HOG, and the first deduction unit 304 and the second deduction units 305-$i$ ($i=1, \ldots, Nf$) may be set as a support vector machine (SVM). In addition to the SVM, another deduction method such as Bayesian network or random forest may be used.

In a case where a method based on the transfer learning is used, it is sufficient when the layer where the image feature amount is obtained is included in an upstream stage with respect to the layer fixed at the time of the transfer learning, and the layers do not necessarily need to be matched with each other. With this configuration, flexibility of the layer where the image feature amount is obtained is increased, and it becomes possible to obtain the more appropriate image feature amount.

In a case where the CNN is used, it is sufficient when the output value of the middle layer which is obtained as the image feature amount is the same, and the CNN where the learning is individually performed without performing the transfer learning may also be used. With this configuration, flexibility of the machine learning is increased, and it also becomes possible to perform the machine learning using the previously obtained image feature amount. Therefore, processing load of the machine learning can be reduced.

The lesion position obtaining unit 302 may automatically detect lesion positions by a related-art image analysis. The lesion position obtaining unit 302 may also obtain one lesion position selected by the user from the automatically detected lesion positions.

The influence degree may be obtained for each element of the channel instead of each channel. In this case, when elements of the channel k are set as (i, j), the first influence degree $\alpha_{d_{ij}}^k$ and the second influence degree $\alpha_{fn_{ij}}^k$ are represented by Expression 5 and Expression 6.

[Math. 5]
$$\alpha_{d_{ij}}^k = \frac{\partial y_d^c}{\partial Y_{ij}^{l,k}} \qquad (5)$$

[Math. 6]
$$\alpha_{fn_{ij}}^k = \frac{\partial y_{fn}^c}{\partial Y_{ij}^{l,k}} \qquad (6)$$

Each of Expression 4 and Expression 5 represents how much the deduction result is changed in a case where the respective element values of the output of the channel k are changed. Since the values obtained by Expression 4 and Expression 5 are not averaged across the entire channel as respectively compared with the values obtained by Expression 1 and Expression 2, the values obtained by Expression 4 and Expression 5 correspond to the value for each element of the channel.

In this case, the matching degree $N_{sn}$ is obtained by Expression 7.

[Math. 7]

$$N_{sn} = \text{count}(Y_{ij}^{l,k} | \alpha_{d_{ij}}^{k} > a_2 \text{ and } \alpha_{d_{ij}}^{k} > a_2) \qquad (7)$$

Where $a_2$ denotes a predetermined constant.

When the influence degree and the matching degree described above are used, in a case where the influence degree of the image feature amount relies on the position on the image, it becomes possible to obtain the matching degree in which the position is taken into account.

As illustrated in Expression 8 and Expression 9, the influence degree may be a rate at which the output of the final layer is changed in a case where the elements (i, j) of the channel k are set as 0.

[Math. 8]

$$\alpha_{d_{ij}}^{k} = \frac{y_d^c - \lim Y_{ij}^{l,k} \to 0 \, y_d^c}{Y_{ij}^{l,k}} \qquad (8)$$

[Math. 9]

$$\alpha_{fn_{ij}}^{k} = \frac{y_{fn}^c - \lim Y_{ij}^{l,k} \to 0 \, y_{fn}^c}{Y_{ij}^{l,k}} \qquad (9)$$

Since the calculation for the above-described influence degree is simple, it becomes possible to reduce the load of the processing for obtaining the influence degree.

In addition, the influence degree may be obtained for each combination of a plurality of image feature amounts. When the influence degree is obtained for each combination, even in a case where the influence occurs by the combination of the plurality of image feature amounts, it becomes possible to obtain the influence degree in which the above-described influence is taken into account.

As illustrated in Expression 10, the matching degree may be a total sum of products of the first influence degree $\alpha_{d_{ij}}^{k}$ and the second influence degree $\alpha_{fn_{ij}}^{k}$.

[Math. 10]

$$P_{sn} = \Sigma_k \Sigma_i \Sigma_j \alpha_{d_{ij}}^{k} \alpha_{fn_{ij}}^{k} \qquad (10)$$

Since the above-described matching degree does not have a threshold, it becomes possible to obtain the matching degree in which all the image feature amounts are taken into account.

The matching degree may be a rate at which the feature amounts having the high first influence degrees and the feature amounts having the high second influence degrees are matched with each other (an expression is not illustrated in the drawing). The matching degree may be a binary value indicating whether or not the matching is established or a discrete value instead of a continuous value.

The case where the matching degree is indicated by the ratio of $N_{sn}$ to $N_f$ in Expression 3 has been described as an example. However, it is sufficient when the matching degree can be represented, and $P_{sn} = N_{sn}$ may be set, for example.

The selection unit 309 may select all the image finding types, and the presentation unit 310 may display a predetermined number of image finding types. The selection unit 309 may also select the image finding type in which the matching degree is higher than or equal to a predetermined value.

The presentation unit 310 may present the matching degree as the reference information together with the image finding. In a case where the matching degree is presented, a numeric value may be presented, or a label or an icon associated with the matching degree may also be presented.

Second Exemplary Embodiment

According to a second exemplary embodiment, the information processing apparatus functioning as the CAD system that performs the diagnosis deduction related to the lung node shadow on the chest X-ray CT image will be described similarly as in the first exemplary embodiment.

In the information processing apparatus according to the first exemplary embodiment, a value obtained by applying any processing to the image is used as the image feature amount. According to the present exemplary embodiment, the image processing apparatus that performs processing while the image itself is regarded as the image feature amount will be described.

It should be noted that the system configuration, the hardware configuration, the configuration of the medical image data, the image finding, the definitions of the values of the diagnosis, the display screen, the main processing, and the diagnosis assistance processing flow of the information processing apparatus according to the present exemplary embodiment are similar to those of the first exemplary embodiment, and descriptions thereof will be described. In addition, unless particularly mentioned, items described according to other exemplary embodiments are assigned with the same reference numerals, and descriptions thereof will be omitted.

According to the present exemplary embodiment, since the image is regarded as the image feature amount, the first influence degree obtaining unit 306 and the second influence degree obtaining units 307-i (i=1, . . . , Nf) respectively obtains a first influence degree $\alpha_{d_{ij}}$ and a second influence degree $\alpha_{fn_{ij}}$ of a pixel value $X_{ij}$ of coordinates (i, j) from Expression 11 and Expression 12.

[Math. 11]

$$\alpha_{d_{ij}} = \frac{y_d^c - \lim X_{ij} \to 128 \, y_d^c}{X_{ij}} \qquad (11)$$

[Math. 12]

$$\alpha_{fn_{ij}} = \frac{y_{fn}^c - \lim X_{ij} \to 128 \, y_{fn}^c}{X_{ij}} \qquad (12)$$

Similarly as in the first exemplary embodiment, the matching degree obtaining unit 308 also obtains the matching degree $P_{sn}$ between the second influence degree $\alpha_{fn_{ij}}$ and the first influence degree $\alpha_{d_{ij}}$ with regard to each of the image finding types (n=1, . . . , Nf) by Expression 13.

[Math. 13]

$$P_{sn} = \frac{N_{sn}}{N_f} \qquad (13)$$

Where $N_{sn}$ denotes the number of the pixels $X_{ij}$ in which both the first influence degree $\alpha_{d_{ij}}$ and the second influence degree $\alpha_{fn_{ij}}$ exceed the predetermined constant $a_3$ and is obtained by Expression 14.

[Math. 14]

$$N_{sn} = \text{count}(X_{ij} | \alpha_{d_{ij}} > a_3 \text{ and } \alpha_{fn_{ij}} > a_3) \quad (14)$$

Herein, count (A|B) represents the number of A satisfying the condition B similarly as in the first exemplary embodiment.

As described above, according to the present exemplary embodiment, even in a case where the diagnosis name is deduced from the medical image, since the image finding highly affecting the deduction result of the diagnosis name can be presented as the reference information, the doctor can determine whether or not the deduction result is useful to the diagnosis.

Modified Example of Second Exemplary Embodiment

The influence degree may be obtained by not only the method described according to the second exemplary embodiment but also a heat map of a technique called "Grad-CAM", for example.

The heat map in "Grad-CAM" is obtained by mapping (imaging) the influence of the input image which affects the deduction result. A heat map $L_{Grad-CAM}^c$ is obtained by Expression 15 and Expression 16.

[Math. 15]

$$\alpha_k^c = \frac{1}{Z} \Sigma_i \Sigma_j \frac{\partial y^c}{\partial A_{ij}^k} \quad (15)$$

[Math. 16]

$$L_{Grad-CAM}^c = ReLU(\Sigma_k \alpha_k^c A^k) \quad (16)$$

Where $y^c$ denotes an output value of the final layer corresponding to a class c and corresponds to an output value of one of nodes (one of circles 909 and 919) of the output layers 909 and 919 in FIG. 9. $A^k$ denotes an output value of the k-th filter of a predetermined layer and corresponds to the k-th output value of the convolutional layer 904 in FIG. 9 (k-th among the squares 904). $A_{ij}^k$ denotes elements of the coordinates (i, j) in the output value of the k-th filter, Z denotes a size of the filter, and ReLU( ) denotes an activating function (ramp function).

When the above-described influence degree is used, since the influence degree with respect to the deduction result of the input image can be obtained by using the feature extracted in the predetermined the convolutional layer, it becomes possible to obtain the influence degree in which the image feature is taken into account. See, for example, Ramprasaath R. Selvaraju, et al., Grad-CAM: Visual Explanations from Deep Networks via Gradient-based Localization, arXiv: 1610.02391v3, 2017.

Modified Examples

According to the above-described exemplary embodiments, the case where the diagnosis assistance related to the lung node shadow on the chest X-ray CT image is performed has been described as an example, but the present invention is not limited to this configuration. The medical image set as the target may be a medical image obtained by using at least one of imaging devices such as a CT device, digital radiography, a magnetic resonance imaging (MRI) device, a single photon emission CT (SPECT) device, a positron emission tomography (PET) device, an ultrasonic diagnostic device, a fundus camera, and a photoacoustic device. The lesion set as the target is not limited to the lung node shadow, and a lesion at any area of a subject may be set as the target.

The present invention can also be realized by processing in which a program that realizes one or more functions of the above-described exemplary embodiments is supplied to a system or an apparatus via a network or a storage medium, and one or more processors in a computer of the system or the apparatus reads out and executes the program. The present invention can also be realized by a circuit (for example, an application specific integrated circuit (an application specific integrated circuit (ASIC))) that realizes one or more functions.

The information processing apparatus according to the above-described respective exemplary embodiments may be realized as a stand-alone apparatus, and a mode may also be adopted in which a plurality of apparatuses are combined with each other in a mutually communicable manner to execute the above-described processing, both of which are included in the exemplary embodiments of the present invention. The above-described processing may be executed by a common server device or a server group. It is sufficient when a plurality of apparatuses constituting the information processing apparatus and the information processing system can communicate at a predetermined communication rate, and the plurality of apparatuses do not necessarily need to exist in the same facility or the same country.

The exemplary embodiments of the present invention includes a mode in which a program of software that realizes the functions of the above-described exemplary embodiments is supplied to the system or the apparatus, and the computer of the system or the apparatus reads out and executes a code of the supplied program.

Therefore, to realize the processing according to the exemplary embodiments by a computer, a program code itself which is installed into the computer is one of the exemplary embodiments of the present invention. Furthermore, the functions of the above-described exemplary embodiments may also be realized by processing in which an OS running on the computer or the like executes part or all of the actual processes on the basis of an instruction included in the program read out by the computer.

Modes obtained by appropriately combining the above-described exemplary embodiments with each other are also included in exemplary embodiments of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-230994, filed Nov. 30, 2017, which is hereby incorporated by reference herein in its entirety.

The invention claimed is:

1. An information processing apparatus comprising:
a first deduction unit configured to deduce a diagnosis name derived from a medical image on a basis of an image feature amount corresponding to a value indicating a feature of the medical image;
a second deduction unit configured to deduce an image finding representing the feature of the medical image on a basis of the image feature amount; and
a presentation unit configured to present the image finding deduced by the second deduction unit affected by an image feature amount common to the image feature amount that has affected the deduction of the diagnosis name by the first deduction unit and the diagnosis name to a user;
a first obtaining unit configured to obtain a first influence degree corresponding to a degree of influence at which the image feature amount affects the deduction result by the first deduction unit;
a second obtaining unit configured to obtain a second influence degree corresponding to a degree of influence at which the image feature amount affects the deduction result by the second deduction unit; and
a third obtaining unit configured to obtain a matching degree corresponding to a degree of matching between the image feature amount that has affected the deduction result by the first deduction unit and the image feature amount that has affected the deduction result by the second deduction unit on a basis of the first influence degree and the second influence degree,
wherein the presentation unit presents the image finding on a basis of the obtained matching degree that is obtained on a basis of the first influence degree and the second influence degree.

2. The information processing apparatus according to claim 1,
wherein the second deduction unit respectively deduces a plurality of image findings representing features of the medical image on a basis of the image feature amount, and
wherein the presentation unit presents the image finding deduced by the second deduction unit affected by the image feature amount common to the image feature amount that has affected the deduction of the diagnosis name by the first deduction unit among the plurality of image findings.

3. The information processing apparatus according to claim 2, further comprising:
a selection unit configured to select the image finding deduced by the second deduction unit affected by the image feature amount common to the image feature amount that has affected the deduction of the diagnosis name by the first deduction unit,
wherein the presentation unit presents the image finding selected by the selection unit.

4. The information processing apparatus according to claim 3,
wherein the second deduction unit includes a plurality of deduction units configured to deduce the image finding for each type of the image findings,
wherein the selection unit selects at least one of the deduction units among the plurality of deduction units, and
wherein the presentation unit presents information of the image finding deduced by the selected deduction unit.

5. The information processing apparatus according to claim 1, wherein the image feature amount that has affected the deduction of the diagnosis name is an image feature amount that has affected the deduction by the first deduction unit at a predetermined degree or above.

6. The information processing apparatus according to claim 1, wherein the third obtaining unit obtains a degree of matching between an image feature amount where the second influence degree is higher than or equal to a predetermined value and an image feature amount where the first influence degree is higher than or equal to the predetermined value as the matching degree.

7. The information processing apparatus according to claim 1, further comprising: a third deduction unit configured to deduce the diagnosis name from the medical image and including the first deduction unit.

8. The information processing apparatus according to claim 7,
wherein the image feature amount is a value obtained from a predetermined stage included in a deduction process in the third deduction unit, and
wherein the first deduction unit performs the deduction in the deduction process in and after the predetermined stage in the third deduction unit.

9. The information processing apparatus according to claim 8, further comprising:
a fourth deduction unit configured to deduce the image finding from the medical image while the deduction process up to at least the predetermined stage is common with the third deduction unit,
wherein the second deduction unit performs the deduction in the deduction process in and after the predetermined stage in the fourth deduction unit.

10. The information processing apparatus according to claim 9, wherein the fourth deduction unit is obtained by performing transfer learning on a basis of the third deduction unit.

11. The information processing apparatus according to claim 1, further comprising:
a fourth deduction unit configured to deduce the image finding from the medical image and including the second deduction unit.

12. The information processing apparatus according to claim 1, wherein the image feature amount is a pixel value of an area having a predetermined size higher than or equal to 1 in the medical image.

13. The information processing apparatus according to claim 1, wherein the presentation unit presents the image finding and the diagnosis name to the user by displaying the image finding and the diagnosis name on a display unit.

14. The information processing apparatus according to claim 1, wherein the presentation unit presents the image finding as reference information with respect to the diagnosis name.

15. An information processing method comprising:
deducing a diagnosis name derived from a medical image on a basis of an image feature amount corresponding to a value indicating a feature of the medical image;
deducing an image finding representing a feature of the medical image on a basis of the image feature amount;
presenting the image finding deduced in the deducing the image finding which is affected by an image feature amount common to the image feature amount that has affected the deduction of the diagnosis name in the deducing the diagnosis name and the diagnosis name to a user;
obtaining a first influence degree corresponding to a degree of influence at which the image feature amount affects the deduction result by the deducing the diagnosis name;
obtaining a second influence degree corresponding to a degree of influence at which the image feature amount affects the deduction result by the deducing the image finding; and
obtaining a matching degree corresponding to a degree of matching between the image feature amount that has affected the deduction result by the deducing the diagnosis name and the image feature amount that has affected the deduction result by the deducing the image finding on a basis of the first influence degree and the second influence degree, wherein the presenting includes presenting the image finding on a basis of the obtained matching degree that is obtained on a basis of the first influence degree and the second influence degree.

16. A non-transitory computer readable medium having stored thereon a program for causing, when executed by a computer, the computer to execute the information processing method according to claim 15.

17. An information processing apparatus comprising:
- a first deduction unit configured to deduce a diagnosis name derived from a medical image on a basis of a plurality of image feature amounts corresponding to values indicating features of the medical image;
- a second deduction unit configured to deduce a plurality of image findings representing the features of the medical image on a basis of the plurality of image feature amounts;
- a first obtaining unit configured to obtain a first influence degree corresponding to a degree of influence at which each of the plurality of image feature amounts affects the deduction result by the first deduction unit;
- a second obtaining unit configured to obtain a second influence degree corresponding to a degree of influence at which each of the plurality of image feature amounts affects the deduction result by the second deduction unit for each image finding;
- a selection unit configured to select at least one of the image findings among the plurality of image findings based on the first influence degree, the second influence degree, and a matching degree between the image feature amount used for the deduction of the diagnosis name and the image feature amount used for the deduction of the image finding; and
- a presentation unit configured to present the diagnosis name deduced by the first deduction unit and the selected image finding to the user.

* * * * *